United States Patent [19]

Sebring

[11] Patent Number: 4,960,271
[45] Date of Patent: Oct. 2, 1990

[54] MEDICAL PATIENT SUPPORT TABLE
[75] Inventor: John P. Sebring, Townsend, Mass.
[73] Assignee: John K. Grady, Harvard, Mass.
[21] Appl. No.: 229,488
[22] Filed: Aug. 8, 1988
[51] Int. Cl.[5] ............................................. A61G 13/00
[52] U.S. Cl. ........................................ 269/323; 5/61; 5/62; 5/63; 378/209; 901/18
[58] Field of Search .................. 269/322–328, 269/60; 254/7 B; 5/61, 62, 63, 64; 378/208, 209, 195, 196; 901/18

[56] References Cited

U.S. PATENT DOCUMENTS

| | | | |
|---|---|---|---|
| 2,663,929 | 12/1953 | Carpenter | 269/60 |
| 3,302,022 | 1/1967 | Brenner et al. | 269/60 |
| 3,396,274 | 8/1968 | Hogan | 269/323 |
| 4,019,059 | 4/1977 | Brundin et al. | 378/209 |
| 4,578,833 | 4/1986 | Vrzalik | 5/61 |
| 4,653,083 | 3/1987 | Rossi | 378/208 |

Primary Examiner—J. J. Hartman
Attorney, Agent, or Firm—James H. Grover

[57] ABSTRACT

A cantilever mounted table for an X-ray patient undergoing procedures requiring tilting the table head to foot or canting the table about its longitudinal axis allows a medical team free axis to one side and an end of the patient, and provides an improved collision sensing switch in the event the table strikes an obstruction below.

5 Claims, 3 Drawing Sheets

MEDICAL PATIENT SUPPORT TABLE

BACKGROUND OF THE INVENTION

This invention involves apparatus for supporting a patient on a table during medical procedures under X-ray observation such as surgery, catheterization and dye angiography, or treatment of a patient in trauma. These procedures usually involve an anesthesiologist and a team of physicians and nurses around a table supporting the patient, and require space for an X-ray tube and receptor to be moved into and out of unlimited positions around the patient, while allowing the medical team free access to at least one side of the table, and allowing the anesthesiologist ready access to the head of the patient. The support apparatus should further be capable of tilting the patient around a transverse axis to raise or lower his head, and canting the patient by rotation generally around his longitudinal axis. However such movements may risk collision of the underside of the patient table with the floor, or equipment on the floor under the table. Collision sensing switches under the table have proven unsatisfactory because they may be inadvertently disabled by straps used to secure the patient to the table.

It has been proposed to support a patient table by a connection offset from the longitudinal axis of the table, but this proposal, although generally satisfactory, causes movement of the patient's head relative to the anesthesiologist during tilting and canting, and increases the possibility of collision below the table.

Accordingly it is an object of the invention to provide patient support apparatus which allows both tilting and canting of the patient by a simplified and more economical and efficient mechanism, and with decreased risk of collision below the patient table.

A further object is to provide patient support apparatus which, without alteration of its components, can be adapted to extend either to the right or left side of its base and standard.

SUMMARY OF THE INVENTION

According to the invention apparatus for supporting a patient during medical procedures comprises a base with an upright standard, a cantilever beam extending horizontally from the standard and having a longitudinal axis, an elongate patient table extending at a right angle to the beam, a rotative attachment of the table to the free end of the beam to cant the table around an axis parallel to the length of the table, and a rotative coupling of the beam to the standard to tilt the table around an axis transverse to the table so that a patient on the table can be both canted about a head to foot axis, and tilted head up or head down about a transverse axis.

Further according to the invention the apparatus includes a motor for turning the beam about its longitudinal axis and tilting the table, an additional motor for canting the table about its longitudinal axis, a crank extending laterally from the beam, a drive link between the motor and the crank, a loose coupling of the link to the crank, and a switch sensing movement of the crank relative to the link to disconnect power to either of the motors when the table collides with an obstruction below.

Still further according to the invention the end of the beam comprises a constant diameter collar extending at right angles to the beam between identical open ends, and a plate rotatively supported in the collar and having means for attachment to the table, the plate being adapted to fit in either open end of the collar so that the table can be rotatively attached at either side of the beam and extend to the right or left of the standard.

DRAWINGS

DESCRIPTION

Figure 1:
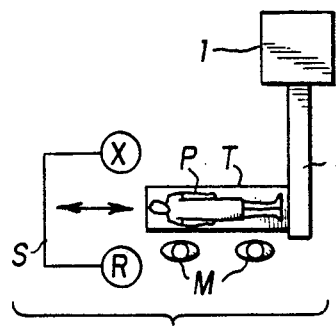
FIGS. 1 and 2 are diagrammatic views of two positions of a patient table relative to a cantilever beam of support apparatus according to the invention.
Figure 2:
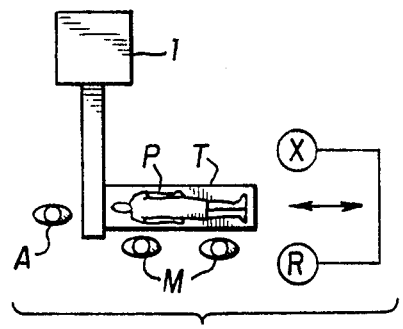

FIGS. 1 and 2 show diagrammatically two alternative overhead dispositions of patient support during X-ray observation. In FIG. 1 the patient P is positioned on a cantilever table T with his feet adjacent the left side of a beam 2 extending from a standard 1. A stand S for an X-ray source X and an X-ray receptor R is moveable from the head toward the feet of the patient. Medical personnel M have the most advantageous access to the head and thorax of patients being catheterized in cardiac procedures with this disposition. But, in other procedures, access by an anesthesiologist to the patient's head would be obstructed by the X-ray stand. Thus hospitals require roughly an equal number of installations with the table extending from the right and left sides of the beam so that the patient can be supported with his head to the beam for access by an anesthesiologist and equipment, and with the foot end of the table free or access by the X-ray stand, or vice versa.

Figure 3:
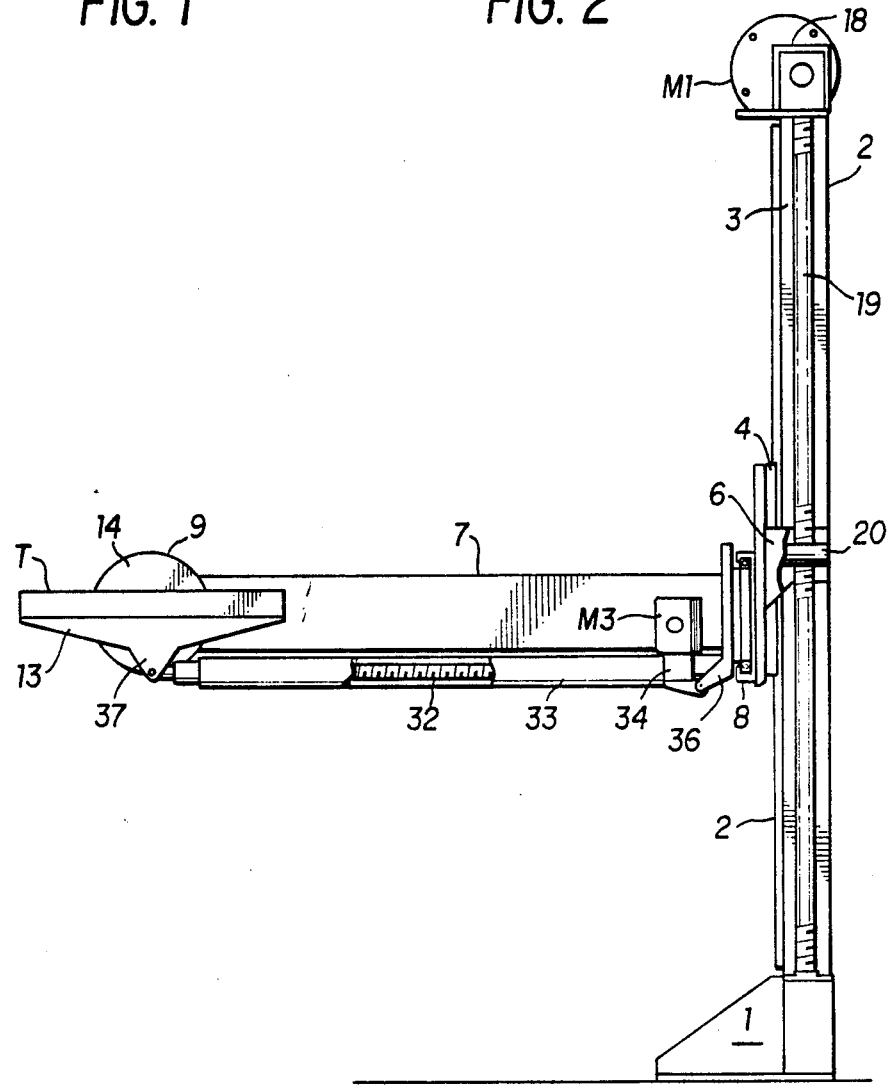
FIG. 3 is a right side elevation of the support apparatus.
Figure 4:
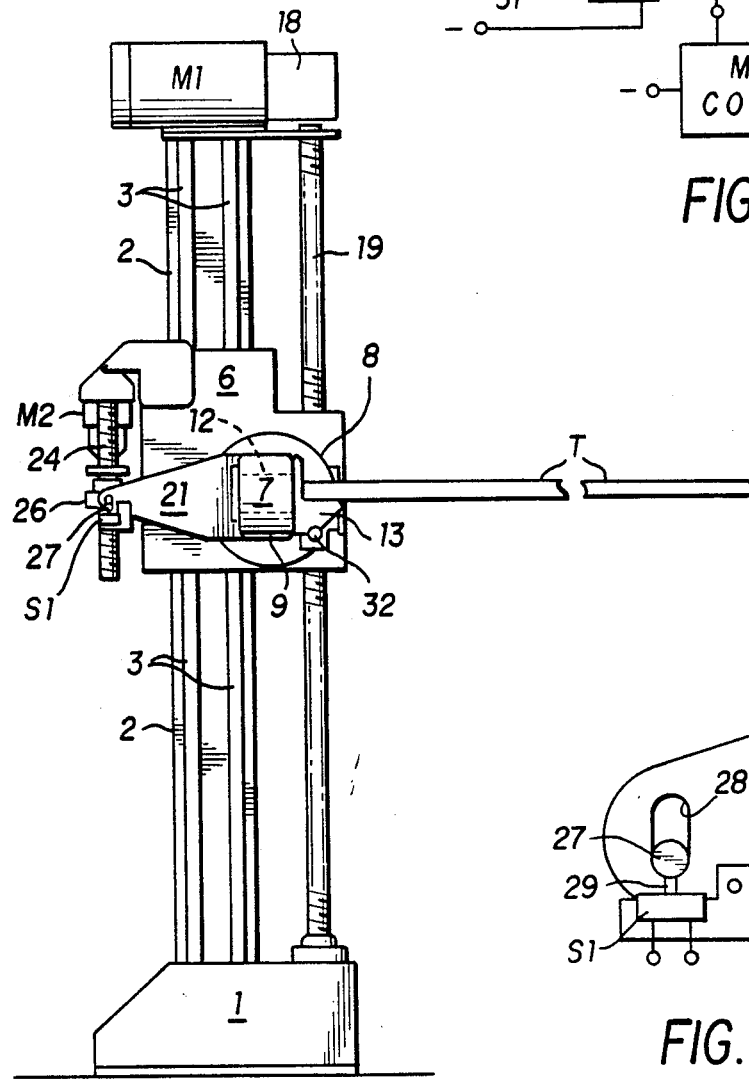
FIG. 4 is an end elevation of the apparatus.
Figure 7:
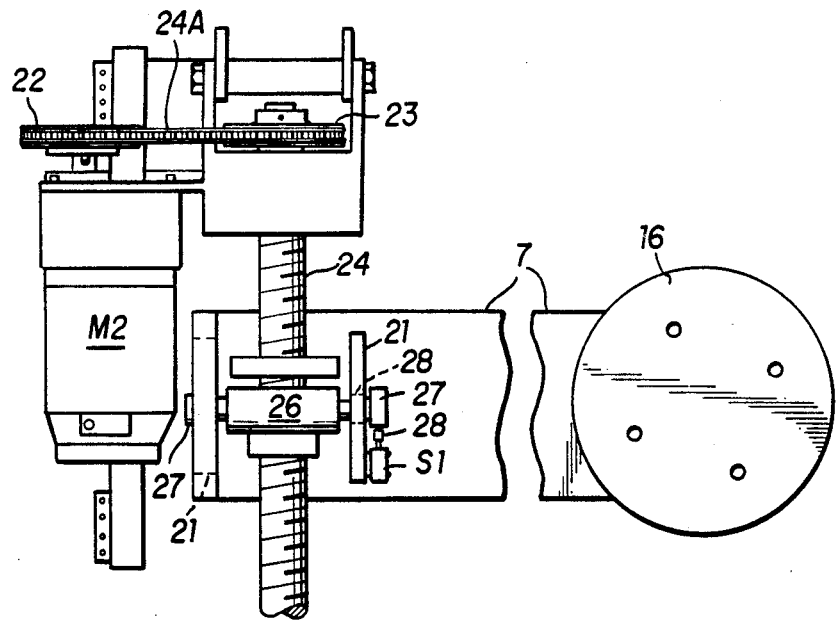
FIG. 7 is an enlarged left side elevation of a detail of FIG. 4.

The structure of apparatus for supporting a patient during the medical procedure is shown generally in FIGS. 3, 4 and 7 and comprises a base 1 anchored on an operating room floor, with an upright standard 2. The standard has vertical rails 3 which are engaged by linear bearings 4 on a carriage 6 which rides up and down on the rails. On the carriage 6 is a heavy duty rotary bearing 8 on which is attached a cantilever beam 7 whose longitudinal axis extends horizontally from the standard. At its free end the cantilever beam 7 forms a cylindrical collar 9 extending at right angles to the beam with a continuous diameter and with identical open ends.

Figure 8:
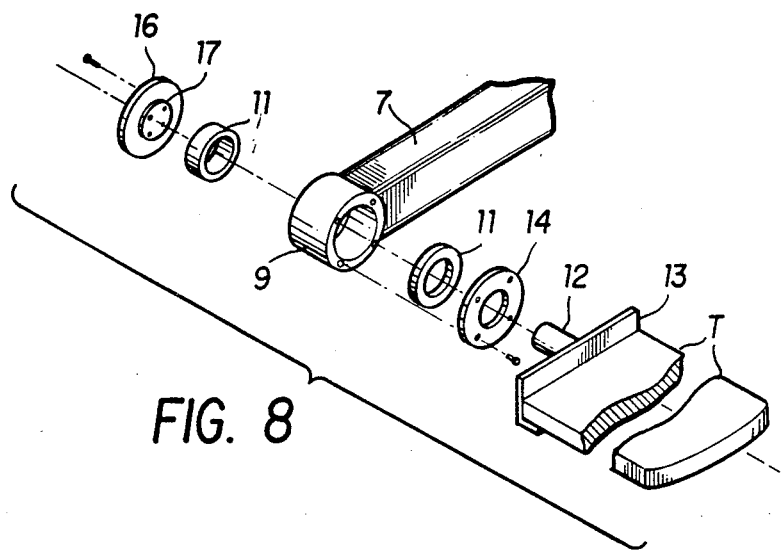
FIG. 8 is an exploded isometric view of the attachment of the patient support table to the cantilever beam.

As shown exploded in FIG. 8 the collar is adapted to receive two rotary bearings 11 in which is journalled the stub shaft 12 of a table bracket 13. One end of the collar is closed by an apertured disk 14 screwed to the collar, and the other end is closed by a circular plate 16 with a circular boss 17 screwed to the stub shaft 12. Secured to the bracket 13 is a table top T adapted to support the patient under examination and extending at a right angle to the longitudinal axis of the beam 7.

Mounted at the top of the standard 2 is a first motor M1 which, through a gear box 18, drives a screw 19 engaging a nut 20 on the carriage so as to raise and lower the carriage and the patient table.

Figure 5:
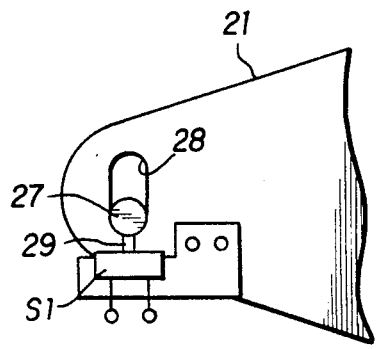
FIG. 5 is an enlarged view of a detail of FIG. 4 showing an electrical collision switch.

As shown particularly in FIGS. 4, 5 and 7, a double crank arm 21 welded to the beam 7 extends laterally from the beam parallel to the carriage 6. A second, tilt motor M2 (FIGS. 4 and 7), through sprockets 22 and 23 and a connecting chain, drives a screw threaded through a nut 26 pivotally secured between the two arms of the crank 21 by a pin 27. When energized the second motor rotates the beam about its longitudinal axis so as to effect Trendelenburg tilting of the patient table about an axis transverse of the patient.

As shown in FIG. 3, a third, cant motor M3 is mounted on the side of the beam from which the table extends. Through a gear box 34 the third motor rotates tubular housing 33. One end of the housing is pivotally anchored in a yoke 36 on the end of the beam, and the other end acts as a nut. One end of the screw 32 is pivotally connected to an extension 37 from the rotating bracket 13 on which the table T is mounted, and the other end of the screw moves within the housing 33. Reversible drive of the third motor M3 rotates the housing and cants the table and patient about an axis which is substantiallY the same as the longitudinal axis of the patient.

Figure 6:
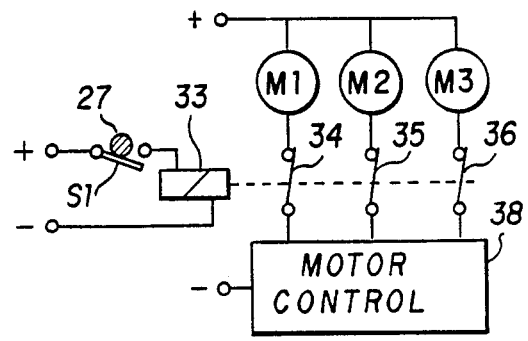
FIG. 6 is an electrical diagram of a circuit connected to the collision switch.

Reverting to FIGS. 5 AND 6, the pin 27 connecting the drive screw 24 of the second motor M2 to the beam crank arms 21 loosely engages in a slot 28 in the crank arms such that the weight of the patient table reflected back through the beam lifts the slot in the crank arms upwardly against the pin 27 at the lower end of the slot. In this position the enlarged end of the pin engages the contact 29 of a spring collision switch S1 attached to one of the crank arms adjacent the slot thereby holding the switch open (FIGS. 4, 5 and 6). If, during a critical procedure with a patient on the table, the table should be driven by any one of the three motors M1, M2 or M3 into collision with any obstruction below the table, the table would he lifted relative to the beam causing the beam crank arm 21 to rotate the collision switch S1 away from engagement with the pin 27 thus allowing the collision switch to close and energize a relay 33. The relay would then open its contacts 34, 35 and 36 between a motor control circuit 37 and the respective motors disabling all of them (with the exception that the motor control circuit would allow the first motor M1 to raise the patient table away from collision).

Thus, no matter which one or combination of the three motors necessary to provide elevation, tilting and canting causes the collision, the single collision switch on the beam crank arm will detect the collision and arrest it instantly.

It should be understood that the present disclosure is for the purpose of illustration only and that the present invention includes all modifications and equivalents falling within the appended claims.

I claim:

1. Apparatus for supporting a patient during medical procedures comprising:
   a base with an upright standard;
   a cantilever beam extending horizontally from the standard and having a longitudinal axis;
   an elongate patient table extending at a right angle to the beam;
   a rotative attachment of the table to the free end of the beam to cant the table around an axis parallel to the length of the table including a rotary bracket journalled in the beam end and attached to the table; and
   a rotative coupling of the beam to the standard to tilt the table around an axis transverse of the table so that a patient on the table can be both canted about a head to foot axis, and tilted head up or head down about a transverse axis;
   wherein the end of the beam comprises a constant diameter collar extending a right angles to the beam between identical open ends, and a plate rotatively supported in the collar and having means for attachment to the table so that the table can be rotatively attached at either side of the beam so as to extend the table to the right or left of the standard.

2. Apparatus for supporting a patient during medical procedures comprising:
   a base with an upright standard;
   a cantilever beam extending horizontally from the standard and having a longitudinal axis;
   an elongate patient table extending at a right angle to the beam;
   a rotative attachment of the table to the free end of the beam to cant the table around an axis parallel to the length of the table; and
   a rotative coupling of the beam to the standard to tilt the table around an axis transverse of the table including a motor for turning the beam about its longitudinal axis through the coupling to the standard so as to tilt the table so that a patient on the table can be both canted about a head to foot axis, and tilted head up or head down about a transverse axis;
   the apparatus including a crank extending laterally from the beam, a drive link between the motor and the crank, a loose coupling of the link to the crank, and a switch sensing movement of the crank relative to the link to disconnect power to the motor when the table collides with an obstruction.

3. Apparatus according to claim 2 including an additional motor on the beam for turning the beam about its longitudinal axis, the switch sensing resulting collision of the table with an obstruction.

4. Apparatus according to claim 2 including a moveable carriage guided vertically of the standard, and an additional motor for raising and lowering the carriage, the switch sensing resulting collision of the carriage with an obstruction.

5. Apparatus for supporting a patient during medical procedures requiring access by medical personnel from alternate left and right sides of the patient, the apparatus comprising:
   a floor base:
   an upright standard mounted on the base and having guide rails extending upwardly therefrom;
   an elevator carriage guided for vertical movement on the rails;
   a first electric motor, on the standard, for raising and lowering the carriage;
   a rotative coupling on the carriage;
   a cantilever beam connected to the coupling and extending horizontally therefrom to turn about its longitudinal axis, the beam having a radial crank arm;
   a second electric motor, on the carriage;
   a drive link between the second electric motor and the crank arm having a loose, lost motion, coupling to the arm;
   a collision switch on the crank arm sensing movement of the crank arm relative to the link;

a collar at the end of the beam having identically annular open ends on an axis normal to the beam;

a plate adapted to be rotatively supported in the collar at either open end;

an elongate patient table attached to the plate normal to the beam and rotatable with the plate to cant the table around an axis parallel to the length of the table;

a third electric motor, on the beam, for rotating the plate and table;

an electric power supply to the motors; and a relay connected to the collision switch and responsive thereto to break the supply of power to the motors, so that collision of the table with an obstruction on downward movement by any of the motors stops such movement.

* * * * *